United States Patent [19]
Hausheer et al.

[11] Patent Number: 6,160,167
[45] Date of Patent: *Dec. 12, 2000

[54] MERCAPTANS AND DISULFIDES

[75] Inventors: Frederick H. Hausheer, Boerne; Kochat Haridas; Qiuli Huang, both of San Antonio, all of Tex.

[73] Assignee: BioNumerik Pharmaceuticals, Inc., San Antonio, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 09/145,384

[22] Filed: Sep. 1, 1998

Related U.S. Application Data

[63] Continuation-in-part of application No. 09/063,592, Apr. 21, 1998, abandoned.

[51] Int. Cl.[7] .............................. C07F 9/38; C07C 309/03
[52] U.S. Cl. ........................... 562/20; 562/101; 562/103; 562/108
[58] Field of Search .............................. 562/30, 101, 103, 562/108, 110, 8, 20

[56] References Cited

U.S. PATENT DOCUMENTS 4,382,040  5/1983  Parr .......................................... 562/110

OTHER PUBLICATIONS

CA:128:252984 abs of WO9811898, Mar. 1998.

CA;90134912 ab of J Bacteriol by Balch 137(1) pp. 256–63, 1979.

CA:112:174633 by Drain in Inorg Chem 29(17)pp. 1428–33, 1990.

CA:75:2092 by Miller in J. Sci. Food Agr. 21(12), pp.616–18, 1970.

*Primary Examiner*—Jean F Vollano
*Attorney, Agent, or Firm*—Thomas J. Dodd

[57] ABSTRACT

This invention relates to novel compositions of matter which either terminate in a sulfhydryl moiety or are disulfides. The compounds also include a terminal sulfonate or phosphonate moiety, and have many uses, such as toxicity reducing agents when administered with many antineoplastic agents.

2 Claims, No Drawings

MERCAPTANS AND DISULFIDES

CROSS-REFERENCE TO RELATED APPLICATIONS

This application is a Continuation-In-Part of U.S. patent application, Ser. No. 09/063,592, filed Apr. 21, 1998 now abandoned.

FIELD OF THE INVENTION

This invention relates to novel derivatives of certain mercapto and disulfide compounds. More specifically, the invention relates to hydroxy and sulfhydryl derivatives of alkane sulfonate compounds useful as protective agents for reducing the undesired toxic effects of certain antineoplastic drugs.

BACKGROUND OF THE INVENTION

Disodium 2,2'-dithiobis ethane sulfonate (Dimesna) is currently in Phase I clinical trials in the United States and abroad as a toxicity reducing agent useful in ameliorating the toxicity of Cisplatin and other antineoplastic agents.

Sodium 2-mercaptoethane sulfonate (Mesna) is an approved drug in the United States and elsewhere for reducing the toxicity of certain antineoplastic alkylating agents, and has been shown to be particularly useful in reducing the acrolein mediated toxicity of cyclophosphamide and ifosfamide.

To date, derivatives of Mesna and Dimesna have been synthesized in which the sulfonate groups have been replaced with phosphonate groups, and the length of the alkane chain has been modified.

Dimesna is the preferred drug for the reduction of the toxicity of platinum complex and other antineoplastic agents because of its stability in the less reactive disulfide form while in the slightly basic environment of the blood.

In the kidney, Dimesna reduces to its monomer, and also forms various heteroconjugates. These species, along with Dimesna, substitute for the toxic hydroxy metabolites of Cisplatin, thus reducing Cisplatin induced nephrotoxicity, while not impairing the activity of the drug against the targeted cancer cells.

SUMMARY OF THE INVENTION

This invention includes novel derivatives of Mesna and Dimesna, and derivatives of the phosphonate analogues of Mesna and Dimesna. The derivatives have the following formula:

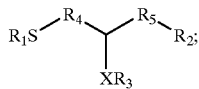
(I)

wherein $R_1$ is hydrogen, lower alkyl, or

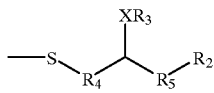
(II)

$R_2$ is sulfonate or phosphonate;
$R_3$ is hydrogen or lower alkyl;
$R_4$ is $C_1$–$C_6$ alkyl or a bond;
$R_5$ is $C_1$–$C_6$ alkyl or a bond; and
X is oxygen or sulfur or X is a bond when $R_1$ is lower alkyl or when $R_4$ and $R_5$ are both bonds;
pharmaceutically acceptable salts thereof.

The novel compounds of this invention will be useful as toxicity reducing agents when administered in combination with many classes of antineoplastic agents. In addition, the compounds will have use as therapeutic agents in the treatment of sickle cell disease, as antidotes for heavy metal poisoning, radiation sickness, free radical elimination, and many others.

This invention also includes pharmaceutical formulations of the formula I compounds. The formulations include the formula I compound as active ingredient, along with one or more pharmaceutically acceptable excipients, diluents and/or solvents. The formulations may be prepared for either oral or parenteral administration to the patient.

Accordingly, it is a principle object of this invention to provide for novel sulfhydryl and disulfide compounds which have pharmaceutical applications in a number of different therapeutic fields.

Another object is to provide for methods of administering the novel sulfhydryl and disulfides to patients in need of therapy.

Other objects will become apparent upon reading the following specification.

DESCRIPTION OF THE PREFERRED EMBODIMENTS

The preferred embodiments herein described are not intended to be exhaustive or to limit the invention to the precise forms disclosed. The are chosen and described to explain the principles of the invention, and its application and practical use to best enable others skilled in the art to follow its teachings.

The compounds of this invention are novel sulfhydryls and disulfides, and have the following general formula I:

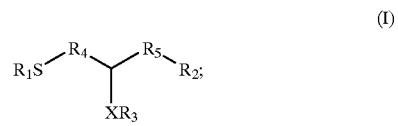
(I)

wherein $R_1$ is hydrogen, lower alkyl, or

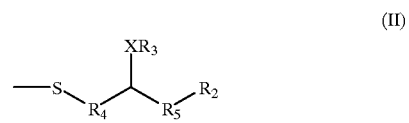
(II)

$R_2$ is sulfonate or phosphonate;
$R_3$ is hydrogen or lower alkyl;
$R_4$ is $C_1$–$C_6$ alkyl or a bond;
$R_5$ is $C_1$–$C_6$ alkyl or a bond; and
X is oxygen or sulfur or X is a bond when $R_1$ is lower alkyl or when $R_4$ and $R_5$ are both bonds;
pharmaceutically acceptable salts thereof.

Preferred compounds of this invention include those where $R_1$ is hydrogen (sulfhydryls) or the formula II moiety (disulfides). Alternatively, preferred compounds may include $R_1$ is a lower alkyl moiety. Preferred compounds also include those wherein $R_2$ is sulfonate, X is oxygen and $R_4$ and $R_5$ are lower alkyl ($C_1$–$C_4$ alkyl). Most preferred are the sodium salts of the sulfonic and phosphonic acid moieties.

The formula I compounds exhibit high water solubility (>150 mg/mL), and are simple and efficient to synthesize and formulate for distribution to patients in either oral or parenteral dose forms. Synthesis of the formula I compounds may be accomplished through any of a number of processes, and the preferred process is outlined below as Scheme I.

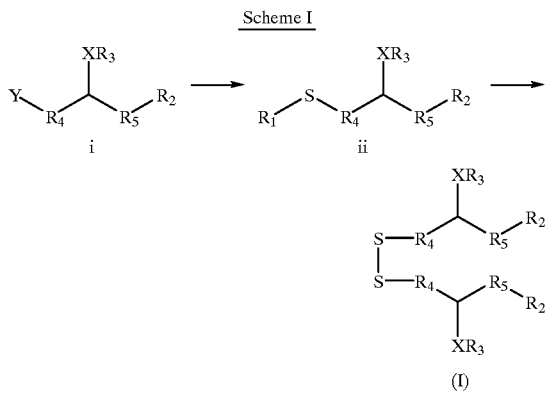

Scheme 1 illustrates the preferred process for synthesizing the sulfhydryl and disulfide compounds of Formula I. In the Scheme, Y represents a leaving group, preferably a halogen moiety, most preferably a chlorine atom, and all of the other variables are as defined above.

As shown in the above Scheme, the Formula I compounds are synthesized by first reacting the starting material (i) with a sulfurating reagent, preferably a hydrosulfide or a polysulfide, most preferably an alkali metal.hydrosulfide, to produce the sulfhydryl compound (ii). The sulfhydryl compound is then oxidized by reacting with an iodine containing agent to form the disulfide of Formula I. Alternatively, the dimerization may be achieved by adding oxygen to the sulfhydryl intermediate, under conditions such as those disclosed in U.S. patent application, Ser. No. 08/935,463, Filed Sep. 24, 1997, incorporated herein by reference. The end compound may also be achieved by a direct dimerization, using the intermediate (ii) as the starting material.

Most preferred conditions and processes for synthesizing the Formula I compounds are disclosed in the Examples which follow the general schemes. Scheme 2 below illustrates the preferred reactions employed in synthesizing the thioether compounds of Formula I.

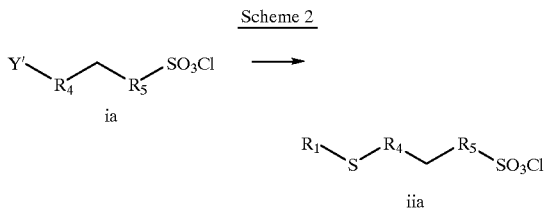

As shown in Scheme 2, the thioether compounds of formula I are synthesized in a two step basic process beginning with starting reagent ia, where Y' is a leaving group, preferably of the same type as Y in Scheme 1. The starting reagent is reacted under basic conditions with a sulfurating agent to displace the leaving group and form thioether iia. The length of the alkyl chain formed is dependent upon the length of the alkyl chain of the sulfurating reagent. In the most preferred compound, $R_1$ is methyl, and the preferred sulfurating reagent is methylmercaptan (methanethiol).

The following examples illustrate preferred methods for synthesizing some the compounds of formula I, with other compounds being synthesized using similar processes. These examples are for illustrative purposes only, and are not to be construed as limiting the invention to the precise conditions or steps disclosed.

EXAMPLE 1

Sodium Mercaptomethyl Sulfonic Acid

To a neat solution of chloromethylsulfonyl chloride (5.0 mL, 8.35 g, 0.056 mol, TCI America) was added water (1.0 mL). The reaction mixture was stirred for 2 h and then added sodium bicarbonate (7.0 g, 1.5 equiv.), sodium hydrosulfide (6.8 g, 3.0 equiv.), along with additional amounts of water (5 mL) to adjust the pH to 8.0. The above mixture was stirred overnight for approximately 15 hours. Solvent was evaporated under reduced pressure to obtain 10.8 g crude sodium mercapto methyl sulfonate. Crude product (2.5 g) was then stirred in DMF for 30 minutes. The residue was filtered off using a sintered funnel. The product (1.8 g) was precipitated out by adding ether, 88% yield.

$^1$H NMR (300 MHz, $D_2O$) $\delta$3.86 ppm.
$^{13}$C NMR (75 MHz, $D_2O$) $\delta$45.5 ppm

EXAMPLE 2

Disodium Dithiobis-methyl Sulfonic Acid

Sodium mercaptomethyl sulfonic acid (1.4 g) in 5 mL water was titrated with aqueous iodine solution containing catalytic amounts of potassium iodide until the color of the reaction solution turned to light yellow, then lyophilized to dryness. The solid was dissolved in 2 mL water and heated to boil. The residue was filtered. Solvent was removed to give 2.93 g product.

$^1$H NMR (300 MHz, $D_2O$) $\delta$4.32 ppm.
$^{13}$C NMR (75 MHz, $D_2O$) $\delta$55.1 ppm.

EXAMPLE 3

Sodium 3-Mercapto-2-Hydroxypropane Sulfonic Acid and Disodium Dithiobis-2-Hydroxy-Propane Sulfonic Acid To sodium 3-chloro-2-hydroxypropanesulfonate hydrate (2.0 g), sodium hydrosulfide hydrate (0.42 g) was added in 10 mL DMF. The mixture was refluxed overnight. When the reaction mixture was cooled down, white solid was isolated, rinsed with ether and acetone to obtain 1.9 g crude sodium 3-mercapto-2-hydroxypropane sulfonate. The crude product was dissolved in water and preferentially precipitated the desired product by adding acetone. The precipitated product was then filtered and dried under vacuum to get 1.04 g of the title compound.

$^1$H NMR (300 MHz, $D_2O$) $\delta$4.28 (m, 1H), 3.28 and 3.24 (d and d, J=4.2 Hz, 1H), 3.13 and 3.08 (d and d, J=7.2 Hz, 1H), 2.98 and 2.93 (d and d, J=4.5 Hz, 1H), 2.86 and 2.80 ppm (d and d, J=6.9 Hz, 1H).
$^{13}$C NMR (75 MHz, $D_2O$) $\delta$67.4, 56.2, 38.7 ppm.

To a small amount of sodium 3-mercapto-2-hydroxypropane sulfonate in $D_2O$ was added excess iodine D₂O solution. Dithiobis-2-hydroxypropane sulfonate disodium salt was obtained. The NMR spectra confirmed the structure.

$^1$H NMR (300 MHz, D₂O) δ4.36 (m, 1H), 3.34 and 3.30 (d and d, J=4.2 Hz, 1H), 3.21 and 3.16 (d and d, J=7.2 Hz, 1H), 3.05 and 3.00 (d and d, J=4.5 Hz, 1H), 2.92 and 2.87 ppm (d and d, J=6.9 Hz, 1H).

$^{13}$C NMR (75 MHz, D₂O) δ67.4, 56.2, 38.68 ppm.

Other compounds falling within the scope of Formula I may be synthesized using slight variants of the above processes. The formula I compounds were analyzed for their ability to displace the hydroxy and aquo moieties of Cisplatin, generally believed to be the toxic metabolites of that molecule. In all formula I cases, displacement of the toxic species of Cisplatin by a sulfhydryl moiety to form a non-toxic compound was predicated by chemical thermodynamic and kinetic properties of the molecules.

The formula I compounds are also predictively efficacious in detoxifying other platinum complex agents, as well as many other antineoplastic drugs, by displacing the free radical moieties generated in vivo by many of these drugs. The compounds will also have usefulness against a variety of other conditions, such as heavy metal poisoning, radiation poisoning, sickle cell disease, and many others where free radicals are commonly present.

The formula I compounds may be administered in any convenient dosage form, with the preferred formulations adapted for oral (PO) or intravenous (IV) administration. Since the solubility of the compounds is greater than 200 mg/mL, formulations are not anticipated to be difficult to make. Further, the formula I compounds have proven to be of very low toxicity, similar to dimesna, which is less toxic than common table salt (Dimesna has not caused a single death in vivo, even at amounts exceeding 5000 mg/kg IV).

Preferred oral formulations include tablets and gelatin capsules, containing an effective amount of the formula I compound, while parenteral formulations are dissolved completely in distilled water prior to administration. Preferred dosage amounts will depend upon the purpose of the administration, with the usual recommended dose ranging from 10 mg/kg to 1,000 mg/kg.

The above description is provide for illustrative purposes only, and is in no way limiting of the invention, whose scope is defined by the following claims.

What is claimed is:

1. A compound having the formula:

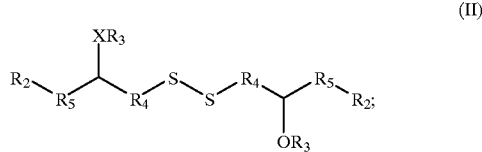

(II)

wherein $R_2$ is sulfonate or phosphonate;

$R_3$ is hydrogen or lower alkyl;

$R_4$ is lower alkyl or a bond;

$R_5$ is lower alkyl;

X is oxygen or a bond; or a pharmaceutically acceptable salt thereof.

2. The compound of claim 1 wherein $R_4$ and $R_5$ are both methylene.

* * * * *